US008598203B2

(12) United States Patent (10) Patent No.: US 8,598,203 B2
Tarcic et al. (45) Date of Patent: Dec. 3, 2013

(54) TREATMENT OF CROHN'S DISEASE WITH LAQUINIMOD

(75) Inventors: Nora Tarcic, Modiin (IL); Asi Haviv, Kvutsat Shiller (IL); Eran Blaugrund, Rehovot (IL); Joel Kaye, Netanya (IL)

(73) Assignee: Teva Pharmaceutical Industries, Ltd., Petach-Tikva (IL)

(*) Notice: Subject to any disclaimer, the term of this patent is extended or adjusted under 35 U.S.C. 154(b) by 314 days.

(21) Appl. No.: 12/804,795

(22) Filed: Jul. 29, 2010

(65) Prior Publication Data

US 2011/0027219 A1 Feb. 3, 2011

Related U.S. Application Data

(60) Provisional application No. 61/273,167, filed on Jul. 30, 2009.

(51) Int. Cl.
*A61K 31/47* (2006.01)
*A61K 9/48* (2006.01)

(52) U.S. Cl.
USPC .......................................... 514/312; 424/452

(58) Field of Classification Search
None
See application file for complete search history.

(56) References Cited

U.S. PATENT DOCUMENTS

| | | | |
|---|---|---|---|
| 3,024,257 A | 3/1962 | Millar et al. | |
| 4,107,310 A | 8/1978 | Allais et al. | |
| 4,547,511 A | 10/1985 | Eriksoo et al. | |
| 4,628,053 A | 12/1986 | Fries et al. | |
| 4,738,971 A | 4/1988 | Eriksoo et al. | |
| 5,716,638 A | 2/1998 | Touitou | |
| 5,912,349 A | 6/1999 | Sih | |
| 6,077,851 A | 6/2000 | Bjork et al. | |
| 6,121,287 A | 9/2000 | Bjork et al. | |
| 6,133,285 A | 10/2000 | Bjork et al. | |
| 6,307,050 B1 | 10/2001 | Kwiatkowski et al. | |
| 6,395,750 B1 | 5/2002 | Hedlund et al. | |
| 6,593,343 B2 | 7/2003 | Bjork et al. | |
| 6,605,616 B1 | 8/2003 | Bjork et al. | |
| 6,696,407 B1 | 2/2004 | Longo et al. | |
| 6,802,422 B2 | 10/2004 | Kalvelage et al. | |
| 6,875,869 B2 | 4/2005 | Jansson | |
| 7,485,311 B2 | 2/2009 | Lue et al. | |
| 7,560,100 B2 | 7/2009 | Pinchasi et al. | |
| 7,560,557 B2 | 7/2009 | Jansson | |
| 7,589,208 B2 | 9/2009 | Jansson et al. | |
| 2002/0173520 A1 | 11/2002 | Bjork et al. | |
| 2003/0087929 A1 | 5/2003 | Kimura et al. | |
| 2003/0119826 A1 | 6/2003 | Manning et al. | |
| 2003/0124187 A1 | 7/2003 | Mention et al. | |
| 2004/0247673 A1 | 12/2004 | Fergione et al. | |
| 2005/0074451 A1 | 4/2005 | Yednock et al. | |
| 2005/0192315 A1 | 9/2005 | Jansson et al. | |
| 2005/0215586 A1 | 9/2005 | Jansson et al. | |
| 2005/0271717 A1 | 12/2005 | Berchielli et al. | |
| 2006/0004019 A1* | 1/2006 | Lieberburg | 514/253.09 |
| 2007/0086979 A1 | 4/2007 | Chevrier et al. | |
| 2007/0088050 A1 | 4/2007 | Frenkel et al. | |
| 2007/0207141 A1 | 9/2007 | Lieberburg et al. | |
| 2007/0231319 A1 | 10/2007 | Yednock et al. | |
| 2007/0280891 A1 | 12/2007 | Tamarkin et al. | |
| 2007/0293537 A1 | 12/2007 | Patashnik et al. | |
| 2008/0044382 A1* | 2/2008 | Lieberburg | 424/85.7 |
| 2008/0063607 A1 | 3/2008 | Tamarkin et al. | |
| 2008/0090897 A1 | 4/2008 | Steiner et al. | |
| 2008/0108641 A1 | 5/2008 | Ajami et al. | |
| 2008/0118553 A1 | 5/2008 | Frenkel et al. | |
| 2008/0166348 A1 | 7/2008 | Kupper et al. | |
| 2008/0206159 A1* | 8/2008 | Tamarkin et al. | 424/45 |
| 2009/0048181 A1 | 2/2009 | Schipper et al. | |
| 2009/0062330 A1 | 3/2009 | Kalafer et al. | |
| 2009/0081259 A1 | 3/2009 | Jonas et al. | |
| 2009/0148462 A1 | 6/2009 | Chevrier et al. | |
| 2009/0156542 A1 | 6/2009 | Purschke et al. | |
| 2009/0162432 A1 | 6/2009 | Safadi et al. | |
| 2009/0221575 A1 | 9/2009 | Gerber et al. | |
| 2009/0232889 A1 | 9/2009 | Jansson et al. | |
| 2010/0055072 A1 | 3/2010 | Gant et al. | |
| 2011/0034508 A1 | 2/2011 | Hayardeny | |
| 2011/0112141 A1 | 5/2011 | Frenkel et al. | |
| 2011/0118308 A1 | 5/2011 | Frenkel et al. | |

(Continued)

FOREIGN PATENT DOCUMENTS

EP 1073639 11/2002
EP 1097139 12/2002

(Continued)

OTHER PUBLICATIONS

NCT00737932, Laquinimod Phase IIa Study in Active Crohn's Disease, Aug. 18, 2008, available at http://www.clinicaltrials.gov/ct2/show/NCT00737932?term=NCT00737932&rank=1 ("NCT00737932", of record).*
Geboes, Crohn's disease, ulcerative colitis or indeterminate colitis—how important is it to differentiate?, Acta Gastroenterol Belg. Apr.-Jun. 2001;64(2):197-200 (Abstract).*
U.S. Appl. No. 12/803,121, filed Jun. 18, 2010, Tarcic et al.
ClinicalTrials.gov. Bethesda (MD): National Library of Medicine (US). Identifier NCT00737932, http://www.clinicaltrials.gov/ct2/show/NCT00737932?term=Crohns&recr=Open&rank=2.
EMEA 2007. Guideline on the Development of New Medicinal Products for the Treatment of Crohn's Disease. CPMP/EWP/2284/99 Rev.1.

(Continued)

*Primary Examiner* — Sreeni Padmanabhan
*Assistant Examiner* — Svetlana M Ivanova
(74) *Attorney, Agent, or Firm* — John P. White; Cooper & Dunham LLP

(57) ABSTRACT

This application provides for a method of treating a subject suffering from Crohn's disease, the method comprising periodically administering to the subject an amount of laquinimod or pharmaceutically acceptable salt thereof effective to treat the subject. This application provides for use of laquinimod in the manufacture of a medicament for treating a subject suffering from Crohn's disease. This application also provides for a pharmaceutical composition comprising laquinimod for use in treating a subject suffering from Crohn's disease.

24 Claims, No Drawings

(56) References Cited

U.S. PATENT DOCUMENTS

| | | |
|---|---|---|
| 2011/0217295 A1 | 9/2011 | Haviv et al. |
| 2011/0218179 A1 | 9/2011 | Haviv et al. |
| 2011/0218203 A1 | 9/2011 | Kaye et al. |
| 2011/0251235 A1 | 10/2011 | Patashnik et al. |
| 2012/0010238 A1 | 1/2012 | Piryatinsky et al. |
| 2012/0010239 A1 | 1/2012 | Fristedt |
| 2012/0142730 A1 | 6/2012 | Tarcic et al. |

FOREIGN PATENT DOCUMENTS

| | | |
|---|---|---|
| EP | 1095021 | 9/2003 |
| EP | 1720531 | 11/2006 |
| EP | 1511732 | 12/2006 |
| WO | WO 99/55678 | 11/1999 |
| WO | WO 03/106424 | 12/2003 |
| WO | WO 2005/074899 | 8/2005 |
| WO | WO 2005074899 A2 * | 8/2005 |
| WO | WO 00/03991 | 1/2007 |
| WO | WO 00/03992 | 1/2007 |
| WO | WO 2007/146331 | 12/2007 |
| WO | WO 2007146331 A1 * | 12/2007 |
| WO | WO 2008/079270 | 7/2008 |
| WO | WO 2008/085484 | 7/2008 |
| WO | WO 2010/057006 | 5/2010 |

OTHER PUBLICATIONS

EMEA 2008. Guideline on the Development of New Medicinal Products for the Treatment of Crohn's Disease. CPMP/EWP/2284/99 Rev.1.

Guindi and Ridell (2004) "Indeterminate Colitis". Journal of Clinical Pathology, 54:1233-1244.

Hendrickson BA, Gokhale R, Cho JH. (2002) "Clinical aspects and pathophysiology of inflammatory bowel disease". Clin Microbiol Rev. 15:79-94.

Teva Press Release, "Laquinimod Demonstrated Significant and Sustained Impact on Multiple Sclerosis Disease Activity", Sep. 18, 2008.

Wen Z and Fiocchi C. (2004) "Inflammatory bowel disease: autoimmune or immune-mediated pathogenesis?" Clin Develop Immunol. 11:195-204.

Wu, George, et al. "Crohn Disease." Emedicine, updated Mar. 17, 2010, retrieved Jul. 27, 2010, available from http://emedicine.medscape.com/article/172940-overview.

U.S. Appl. No. 12/806,275, filed Aug. 9, 2010, Liat Hayardeny.

U.S. Appl. No. 12/962,595, filed Dec. 7, 2010, Nora Tarcic, et al.

Written Opinion of the International Searching Authority issued Oct. 5, 2010 in connection with PCT International Application No. PCT/US2010/02194, filed Aug. 9, 2010.

PCT International Search Report issued Oct. 5, 2010 in connection with PCT International Application No. PCT/US2010/02194, filed Aug. 9, 2010.

Written Opinion of the International Searching Authority issued Sep. 7, 2010 in connection with PCT International Application No. PCT/US2010/02129 filed Jul. 29, 2010.

PCT International Search Report issued Sep. 7, 2010 in connection with PCT International Application No. PCT/US2010/02129 filed Jul. 29, 2010.

Written Opinion of the International Searching Authority issued Aug. 19, 2010 in connection with PCT International Application No. PCT/US2010/01759, filed Jun. 18, 2010.

PCT International Search Report issued Aug. 19, 2010 in connection with PCT International Application No. PCT/US2010/01759, filed Jun. 18, 2010.

Boneschi, et al. (2003) "Effects of glatiramer acetate on relapse rate and accumulated disbility . . . " Multi Scler. 9(4):349-355.

Friedman S, Blumberg RS. Inflammatory Bowel Disease. In: Braunwald E., Fauci AS . . . Harrison's Principles of Internal Medicine.New York: McGraw-Hill Professional, 2001:1679-92.

Makar, et al. (2008) "Brain derived neurotrophic factor treatment reduces . . . " Journal of the Neurological Sciences. 270(1-2):70-76.

Mix, et al. (2008) "Animal models of multiple sclerosis for the development and validation of novel therapies—potential and limitations." Journal of Neurology. 255(6):7-14.

Polman, et al., (2005) "Treatment with laquinimod reduces development of active MRI lesions in relapsing MS", Neurology. 64:987-991.

Sandberg-Wollheim, et al. (2005) "48-Week Open Safety Study with a High-Dose Oral . . . " Therapy-Immunomodulation—Part II, Sep. 30, 2005, 15:30-17:00 (Abstract only).

PCT International Preliminary Report on Patentability issued Feb. 14, 2012 in connection with PCT International Application No. PCT/US2010/002194.

Extended European Search Report issued Jan. 10, 2013 in connection with European Patent Application No. 10804826.5.

International Seach Report issued Apr. 9, 2013 in connection with PCT International Application No. PCT/US13/24356.

Written Opinion of the International Searching Authority issued Apr. 9, 2013 in connection with PCT International Application No. PCT/US13/24356.

Mar. 26, 2013 Office Action issued in connection with Chinese Patent Application No. 201080039833.9.

* cited by examiner

TREATMENT OF CROHN'S DISEASE WITH LAQUINIMOD

This application claims the benefit of U.S. Provisional Application No. 61/273,167, filed Jul. 30, 2009, the entire content of which is hereby incorporated by reference herein.

Throughout this application various publications are referenced. The disclosures of these publications in their entireties are hereby incorporated by reference into this application in order to more fully describe the state of the art to which this invention pertains.

BACKGROUND

Crohn's disease (CD) and Ulcerative Colitis (UC) are the two major types of Inflammatory Bowel Disease (IBD)—a generic classification for a group of nonspecific, idiopathic inflammatory disorders of, the gastrointestinal. (GI) tract which also includes Indeterminate Colitis (IC). Indeterminate Colitis refers to the up to 15% of IBD cases where distinguishing between CD and UC is impossible. (Kasper, 2008) Both CD and UC tend to be chronic in nature and run a course characterized by exacerbations and remissions.

CD may occur in any part of the GI tract, but most commonly affects the distal ileum and colon. It is characterized by transmural inflammation of the gastrointestinal wall, interspersed with "skip" areas of normal tissue, leading to the characteristic endoscopic and radiographic appearance of the disease. In about half the cases, biopsy specimens reveal the pathognomonic histology of noncaseating granulomas (Friedman, 2001).

Although CD usually presents as acute or chronic bowel inflammation, the inflammatory process evolves toward one or two patterns of disease: a fibrostenotic-obstructing pattern or a penetrating-fistulous pattern, each with different treatments and prognoses (Friedman, 2001).

The characteristic inflammatory presentation of Crohn's disease is of abdominal pain, diarrhea, fever and weight loss which may be complicated by intestinal fistulization, obstruction, or both. Fistula formation may occur to the adjacent bowel, the skin, the urinary bladder, or other locations. Obstruction, if present, is initially intermittent due to bowel wall edema and spasm; further progression may lead to chronic scarring and stricture formation. Perianal disease is common and may manifest as anal fissure, perianal fistula, or abscess (Friedman, 2001; Wu, 2007).

Extra-intestinal manifestations may also occur and include joint inflammation (e.g., peripheral arthritis, ankylosing spondylitis), skin lesions (e.g., erythema nodosum, pyoderma gangrenosum), ocular involvement (e.g., iritis, uveitis) and liver disorders (e.g., hepatic steatosis, primary sclerosing cholanitis) (Friedman, 2001; Wu, 2007).

The incidence of CD varies within different geographic areas. Northern countries such as the US, UK, Norway and Sweden have the highest rates. The incidence of CD in the US is approximately 7 per 100,000. Countries in southern Europe, South Africa and Australia have lower incidence rates of 0.9 to 3.1 per 100,000. The disease is rare in Asia and South America (Friedman, 2001).

The peak age of onset of Crohn's disease occurs between the ages of 15 and 30 years, with a second peak of occurrence between the ages of 60-80 years (Friedman, 2001).

The fundamental cause of CD is unknown. There are four basic factors affecting the pathophysiology of CD: genetics, immune dysregulation, epithelial barrier dysfunction and the constitution of microbial flora. Evidence suggests that genetic predisposition leads to an unregulated intestinal immune response to an environmental, dietary or infectious agent (Friedman, 2001; Wen, 2004). A number of studies suggest that CD is a T-helper 1 (Th-1) mediated disease and that the excessive Th1-cell activity leading to the production of a wide range of proinflammatory cytokines [including interleukin (IL)-1, IL-2 and tumor necrosis factor (TNF)-$\alpha$] and an imbalance between proinflammatory and anti-inflammatory reactivity, is a critical component of CD (Hendrickson, 2002). However, no inciting antigen has been identified.

In the absence of a key diagnostic test, the diagnosis of Crohn's disease is based on endoscopic, radiographic and pathological findings documenting focal, asymmetric transmural or granulomatous features. Laboratory abnormalities include non-specific markers of inflammation such as elevated sedimentation rate and C-reactive protein (CRP). In more severe cases, finding may include hypoalbuminemia, anemia, and leukkocytosis (Friedman, 2001; Wu, 2007).

There is no definitive treatment or cure for CD. The major therapeutic goals are the reduction of signs and symptoms, induction and maintenance of remission and most importantly, the prevention of disease progression and complications.

Sulfasalazine and other 5-aminosalicylic acid agents, antibiotics such as metronidazole and ciprofloxacin, corticosteroids, immunosupressors such as azathioprine and 6-mercaptopurine and biologic agents such as anti-TNF$\alpha$ agents and anti-integrins, that prevents leukocyte infiltration have shown to be useful in the induction of remission and/or in its maintenance (Targan, 1977; Hanauer, 2002; Colombel, 2007; Ghosh, 2003; Sandborn, 2005; Schreiber, 2005; Schreiber, 2007; Kozuch, 2008). Many of these medicinal products, however, are only moderate efficacious and are associated with challenging side effects (Hommes, 2003; Thomas, 2004; Colombel, 2004; Van Assche, 2005; Vermeire, 2003; Sweetman, 2006). In addition, the newer biologic agents have a relatively inconvenient parenteral route of administration. There is, therefore, a definite need for alternative therapies with better risk-benefit profiles and a more convenient route of administration than the currently available options.

Disclosed is a method of treating Crohn's disease using laquinimod. Laquinimod is a novel synthetic compound with high oral bioavailability, which has been suggested as an oral formulation for Relapsing Remitting Multiple Sclerosis (MS). Laquinimod and its sodium salt form are described, for example, in U.S. Pat. No. 6,077,851. The effects of laquinimod on Crohn's disease have not been reported.

SUMMARY OF THE INVENTION

This application provides for a method of treating a subject suffering from Crohn's disease, the method comprising periodically administering to the subject an amount of laquinimod or pharmaceutically acceptable salt thereof effective to treat the subject.

This application provides for use of laquinimod in the manufacture of a medicament for treating a subject suffering from Crohn's disease.

This application also provides for a pharmaceutical composition comprising laquinimod for use in treating a subject suffering from Crohn's disease.

DETAILED DESCRIPTION OF THE INVENTION

This application provides for a method of treating a subject suffering from Crohn's disease, the method comprising periodically administering to the subject an amount of laquinimod or pharmaceutically acceptable salt thereof effective to treat the subject.

In one embodiment, the amount of laquinimod is effective to reduce a symptom of Crohn's disease in the subject, induce clinical response, induce or maintain clinical remission, inhibit disease progression, or inhibit a disease complication in the subject.

In another embodiment, the amount of laquinimod is effective to reduce the Crohn's Disease Activity Index score of the subject, lower the C-Reactive Protein level of the subject, lower the fecal calprotein level of the subject, or reduce the number of open draining fistulas in the subject.

In one embodiment, the amount of laquinimod is effective to lower the subject's dependence on steroids.

In one embodiment, the Crohn's Disease Activity Index score of the subject is reduced by at least 100 points. In another embodiment, the Crohn's Disease Activity Index score of the subject is reduced to under 150.

In one embodiment, the number of open draining fistulas in the subject is decreased at least 50% as compared to prior to initiation of the periodic administration.

In one embodiment, the periodic administration is oral.

In one embodiment, the amount is administered by a unit dose of 0.5 mg of laquinimod. In another embodiment, the periodic administration is daily administration. In another embodiment, the amount of laquinimod is 0.5-2.0 mg/day. In another embodiment, the amount of laquinimod is 1.0 mg/day. In another embodiment, the amount of laquinimod is 1.5 mg/day. In yet another embodiment, the amount of laquinimod is 2.0 mg/day.

In one embodiment, a loading dose of an amount different from the intended dose is administered for a period of time at the start of the periodic administration. In another embodiment, a loading dose of double the amount of the intended dose is administered for a period of time at the start of the periodic administration. In another embodiment, a loading dose of an amount different from the intended dose is administered for two days at the start of the periodic administration. In yet another embodiment, a loading dose of double the amount of the intended dose is administered for two days at the start of the periodic administration.

In one embodiment, the subject had active moderate to severe Crohn's disease prior to the administration of laquinimod. In another embodiment, the subject had a Crohn's Disease Activity Index score of 220-450 prior to the administration of laquinimod. In another embodiment, the subject had a C-Reactive Protein level of above 5 mg/L prior to the administration of laquinimod. In another embodiment, diagnosis of the subject prior to administration excluded Indeterminate Colitis. In yet another embodiment, diagnosis of the subject prior to administration excluded Ulcerative Colitis.

In one embodiment, the periodic administration continues for 8 weeks or more.

In one embodiment, the laquinimod is in the form of laquinimod sodium.

In one embodiment, the subject is a human.

In one embodiment, the method further comprises administration of 5-aminosalicylic acid, antibiotics, corticosteroids, immunosuppressors, or biologic agents including TNFα agents and anti-integrins.

This application also provides for use of laquinimod in the manufacture of a medicament for treating a subject suffering from Crohn's disease.

This application also provides for a pharmaceutical composition comprising laquinimod for use in treating a subject suffering from Crohn's disease.

All combinations of the various elements described herein are within the scope of the invention.

A pharmaceutically acceptable salt of laquinimod as used in this application includes lithium, sodium, potassium, magnesium, calcium, manganese, copper, zinc, aluminum and iron. Salt formulations of laquinimod and the process for preparing the same are described, e.g., in U.S. Patent Application Publication No. 2005/0192315 and PCT International Application Publication No. WO 2005/074899, each of which is hereby incorporated by reference into this application.

A dosage unit may comprise a single compound or mixtures of compounds thereof. A dosage unit can be prepared for oral dosage forms, such as tablets, capsules, pills, powders, and granules.

Laquinimod can be administered in admixture with suitable pharmaceutical diluents, extenders, excipients, or carriers (collectively referred to herein as a pharmaceutically acceptable carrier) suitably selected with respect to the intended form of administration and as consistent with conventional pharmaceutical practices. The unit will be in a form suitable for oral administration. Laquinimod can be administered alone but is generally mixed with a pharmaceutically acceptable carrier, and co-administered in the form of a tablet or capsule, liposome, or as an agglomerated powder. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents flow-inducing agents, and melting agents.

Specific examples of the techniques, pharmaceutically acceptable carriers and excipients that may be used to formulate oral dosage forms of the present invention are described, e.g., in U.S. Patent Application Publication No. 2005/0192315, PCT International Application Publication Nos. WO 2005/074899, WO 2007/047863, and WO/2007/146248, each of which is hereby incorporated by reference into this application.

General techniques and compositions for making dosage forms useful in the present invention are described-in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol. 40 (Gilbert S. Banker, Christopher T. Rhodes, Eds.). These references in their entireties are hereby incorporated by reference into this application.

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, dicalcium phosphate, calcium sulfate, mannitol, sorbitol, microcrystalline cellulose and the like. Suitable binders include starch, gelatin, natural sugars such as glucose or beta-lactose, corn starch, natural and synthetic gums such as acacia, tragacanth, or sodium alginate, povidone, carboxymethylcellulose, polyethylene glycol, waxes, and the like. Lubricants used in these dosage forms include sodium oleate, sodium stearate, sodium benzoate, sodium acetate, sodium chloride, stearic acid, sodium stearyl fumarate, talc and the like. Disintegrators include, without limitation, starch, methyl cellulose, agar, bentonite, xanthan gum, croscarmellose sodium, sodium starch glycolate and the like.

Terms

As used herein, and unless stated otherwise, each of the following terms shall have the definition set forth below.

An "amount" or "dose" of laquinimod as measured in milligrams refers to the milligrams of laquinimod acid present in a preparation, regardless of the form of the preparation.

As used herein, a "loading dose" refers to an initial higher dose of a drug that may be given at the beginning of a course of treatment before dropping down to a lower "intended dose" or "maintenance dose".

As used herein, "Crohn's Disease Activity Index" or "CDAI" is a research tool developed by WR Best and colleagues from the Midwest Regional Health Center in Illinois, in 1976 (Best, 1976) to quantify the symptoms of patients with Crohn's disease. The index is the most widely used instrument for evaluation of Crohn's disease activity (Best, 1976; Best, 1979; Sandborn, 2002) and consists of eight factors/variables.

The eight variables are summed after adjustment with a weighting factor. The components of the CDAI and weighting factors are shown in the following table:

| Clinical or laboratory variable | Weighting factor |
|---|---|
| Number of liquid or soft stools (sum of each day for 7 days) | ×2 |
| Abdominal pain (graded from 0-3 on severity) (sum of each day for 7 days) | ×5 |
| General well being, subjectively assessed from 0 (well) to 4 (terrible) (sum of each day for 7 days) | ×7 |
| Presence of Crohn's disease complications | ×20 |
| Use of dyphenoxylate or loperamide for diarrhea during the past week (0 = no, 1 = yes) | ×30 |
| Presence of an abdominal mass (0 as none, 2 as questionable, 5 as definite) | ×10 |
| Absolute deviation of Hematocrit from 47% in men and 42% in women | ×6 |
| Percentage deviation from standard weight | ×1 |

The first 4 of these variables and the presence of fever above 37.8° C., are self-reported in subject diaries, the remaining 4 are assessed at the study visit. Height and standard weight assessment are based on standard height-weight tables.

Total CDAI scores range from 0 to approximately 600 where the higher the score, the more active the disease. A CDAI score of less than 150 points denotes "clinical remission" of the Crohn's disease, of between 150 to 219 points denotes "active mild Crohn's disease", of between 220 to 450 points denotes "active moderate Crohn's disease" and of more than 450 points denotes "active severe Crohn's disease".

"Clinical response" means that the subject's Crohn's disease symptoms have decreased in severity and/or in number. "Clinical remission" means that the subject's Crohn's disease symptoms have decreased in severity and/or in number to below a defined level, e.g., below 150 points on the CDAI scale. "Clinical remission" and "clinical response" may be measured in accordance with the EMEA draft guidelines on the development of new medicinal products for the treatment of Crohn's disease. The EMEA guidelines define "clinical remission" as reduction in CDAI score to a total score below 150 points and "clinical response" as if remission has been achieved or a reduction of at least 100 points in the total CDAI score has been observed, compared to baseline at the end of the treatment period (EMEA, 2007).

"Indeterminate Colitis" or "IC" is used clinically in patients with some form of Inflammatory Bowel Disease in whom a definite diagnosis of either Ulcerative Colitis (UC) or Crohn's Disease (CD) has not been made, either on colonoscopy or colonic biopsy before colectomy. Although some patients diagnosed with Indeterminate Colitis go on to develop UC or CD, studies have shown that over a median follow up period of 10 years, many patients retain diagnosis of Indeterminate Colitis. (Guindi, 2004)

"Inhibition" of disease progression or disease complication in a subject means preventing or reducing the disease progression and/or disease complication in the subject.

As used herein, "C-reactive protein" or "CRP" is an inflammatory mediator whose levels are raised under conditions of acute inflammatory recurrence and rapidly normalize once the inflammation subsides. Crohn's disease may be characterized according to disease behavior: predominantly nonstricturing nonpenetrating (inflammatory), stricturing or penetrating (Silverberg, 2005). The origin of symptoms such as diarrhea, fatigue, or abdominal pain (affects the CDAI score) may be multifactorial and does not necessarily correlate with the existence of prominent inflammatory lesions of the gastrointestinal (GI) tract. Predominantly nonstricturing nonpenetrating (inflammatory) Crohn's disease may be characterized by high CRP levels. Therefore the CRP may serve as a surrogate marker to monitor inflammatory disease activity and response to treatment (Solem, 2005; Denis, 2007; Chamouard, 2006).

As used herein, "calprotectin" is a calcium and zinc binding anti-microbial protein released by granulocytes. This protein can be detected in stool and its concentration reflects the number of polymorphonuclear leukocytes (PMN), migrating into the gut lumen. It is therefore considered a bio-marker for intestinal inflammation.

As used herein, "effective" when referring to an amount of laquinimod refers to the quantity of a laquinimod that is sufficient to yield a desired therapeutic response without undue adverse side effects (such as toxicity, irritation, or allergic response) commensurate with a reasonable benefit/risk ratio when used in the manner of this invention.

As used herein, "treating" encompasses, e.g., inducing inhibition, regression, or stasis of the disorder.

As used herein, "pharmaceutically acceptable carrier" refers to a carrier or excipient that is suitable for use with humans and/or animals without undue adverse side effects (such as toxicity, irritation, and allergic response) commensurate with a reasonable benefit/risk ratio. It can be a pharmaceutically acceptable solvent, suspending agent or vehicle, for delivering the instant compounds to the subject.

It is understood that where a parameter range is provided, all integers within that range, and tenths thereof, are also provided by the invention. For example, "5-10%" includes 5.0%, 5.1%, 5.2%, 5.3%, 5.4% etc. up to 10.0%.

This invention will be better understood by reference to the Experimental Details which follow, but those skilled in the art will readily appreciate that the specific experiments detailed are only illustrative of the invention as described more fully in the claims which follow thereafter.

Experimental Details

Example 1

Clinical Trial (Phase IIa)—Assessment of Oral Laquinimod in Active Moderate to Severe Crohn's Disease A phase IIa, multicenter, randomized, double-blind, placebo-controlled, sequential cohorts, dose range finding study is conducted to evaluate escalating doses of Laquinimod in active moderate to severe Crohn's disease.

Study Title

A Phase IIa, Multicenter, Randomized, Double-Blind, Placebo-Controlled, Sequential Cohorts, Dose Range Finding Study to Evaluate the Safety, Tolerability and Clinical Effect of Escalating Doses of Laquinimod in Active Moderate to Severe Crohn's disease.

Participating Countries and Number of Sites

Europe (Belgium, France, Italy, Netherlands, Spain, Poland and UK), Israel and South Africa in approximately 50 sites.

Number of Subjects

There are 4 distinct sequential cohorts with approximately 45 subjects for each of the cohorts, randomized in a 2:1 ratio (~30 subjects on laquinimod and ~15 on placebo). Overall up to ~180 Crohn's disease patients are enrolled.

Investigational Medicinal Product (IMP) & Dosage

One or more capsules containing laquinimod 0.5 mg or matching placebo are administered orally once daily:
$1^{st}$ cohort—laquinimod 0.5 mg (1×0.5) or matching placebo;
$2^{nd}$ cohort—laquinimod 1.0 mg (2×0.5) or matching placebo;
$3^{rd}$ cohort—laquinimod 1.5 mg (3×0.5) or matching placebo; and
$4^{th}$ cohort—laquinimod 2.0 mg (4×0.5) or matching placebo.

The 0.5 mg laquinimod capsules were prepared using 0.534 mg of laquinimod sodium per capsule (which is equivalent to 0.5 mg of laquinimod acid). The capsules were prepared using a blend proportional to the 0.6 mg capsules described in PCT International Application No. PCT/US2007/013721 (WO 2007/146248). The capsules were prepared according to the method described in PCT International Application No. PCT/US2007/013721 (WO 2007/146248), which is hereby incorporated by reference into this application.

A loading dose regimen of double the maintenance/intended dose is given during the first two days of study drug treatment. Thereafter, starting on day 3, the daily maintenance/intended dose is administered.

Table 1 summarizes the number of capsules and total dose which are administered daily for each of the 4 study cohorts, at different time points throughout the treatment period. "BID" indicates that the dose is administered twice daily. "QD" indicates that the dose is administered once daily.

Subjects are required to maintain CDAI diary cards for each day of the screening period and, if randomized, on each day of the treatment and follow-up period. The scores obtained from the seven consecutive diaries completed prior to the baseline visit and to each of weeks 1, 2, 4, 6, 8 and 12 contribute to a total CDAI score at each of the time points.

Allowed previous standard of care treatment is kept stable throughout the study (including the follow-up period, as defined herein).

Study Duration

Each Cohort (Dose Group) is Evaluated for Up to 14 Weeks
Screening: between 1-2 weeks
Treatment period: 8 weeks
Follow-up period: 4 weeks Study Population Moderate to severe Crohn's disease (CD) subjects as determined by a Crohn's Disease Activity Index (CDAI) score of 220-450 (inclusive).

Study Design

This Phase IIa, randomized, double-blind, placebo-controlled, sequential cohorts, dose range finding study to assess the safety tolerability and clinical effect of escalating dose of laquinimod in active moderate to severe Crohn's disease is the first study to assess the safety, tolerability and efficacy of laquinimod in active CD subjects.

This study investigates laquinimod doses at 0.5, 1.0, 1.5 and 2.0 mg daily. Each dose is studied sequentially in a distinct cohort.

Subjects are assessed for study eligibility 1 to 2 weeks prior to baseline.

Approximately 45 eligible subjects are assigned to each cohort. Subjects are randomized in a 2:1 ratio for either of the following treatment arms:
1. Oral laquinimod (~30 subjects).
2. Matching oral placebo (~15 subjects).

Each successive cohort is screened/randomized only when the two conditions below have been met:
1. Randomization of at least 45 subjects for the preceding cohort and closure of screening and randomization of the preceding cohort.
2. Decision of a safety committee to proceed to the next dose level.

This decision is based on data review of at least 15 subjects who have completed at least 4 weeks of treatment in the preceding cohort, as well as all other data obtained in the study for any of the preceding cohorts.

All study investigators are informed when screening and/or randomization are closed for the preceding cohort and opened for the next cohort/dose level. All subjects in screening phase are allowed to be randomized (if eligible) to the preceding cohort or the next cohort, whichever is opened at randomization/baseline visit.

The safety committee may determine at any of these safety evaluations, that a Dose Limiting Toxicity (DLT) has been reached. Criteria for DLT are not predefined and are based solely on the safety committee's best medical judgment.

TABLE 1

| | Day 1 | | Day 2 | | Day 3 onwards | |
|---|---|---|---|---|---|---|
| Cohort | 0.5 mg/plc capsules/day | Dose/day | 0.5 mg/plc capsules/day | Dose/day | 0.5 mg/plc capsules/day | Dose/day |
| 1 | 1 + 1 (BID) | 1 mg/placebo | 1 + 1 (BID) | 1 mg/placebo | 1 (QD) | 0.5 mg/placeo |
| 2 | 2 + 2 (BID) | 2 mg/placebo | 2 + 2 (BID) | 2 mg/placebo | 2 (QD) | 1 mg/placeo |
| 3 | 3 + 3 (BID) | 3 mg/placebo | 3 + 3 (BID) | 3 mg/placebo | 3 (QD) | 1.5 mg/placeo |
| 4 | 4 + 4 (BID) | 4 mg/placebo | 4 + 4 (BID) | 4 mg/placebo | 4 (QD) | 2 mg/placeo |

In case a dose limiting toxicity has been reached the following decision options exist for the safety committee:
1. Complete the current cohort without proceeding to the next dose level/cohort; and
2. Terminate the study immediately.

Scheduled in-clinic visits are conducted at screening, baseline and at weeks 1, 2, 4, 6 and 8. Treatment with laquinimod/placebo are discontinued on visit week 8 and a follow-up/study completion visit is conducted at week 12. Subjects who early-discontinues study drug prior to visit week 8 go to follow-up termination visit within 4 weeks (28 days) of study drug discontinuation.

Unscheduled visits for safety or for any other reason may be conducted at any time during the study.

During the study period the CDAI score is assessed in addition to routine safety laboratory tests and PK analysis.

Based on previous pharmacokinetic studies, laquinimod reaches steady state following approximately 10-12 days of daily maintenance dosing. In order to decrease thee time to steady state and potentially decrease time to response, a loading dose regimen described below is used to allow steady state levels to be reached in approximately 6-7 days.

A loading dose regimen of the study drug is given during the first two days of treatment (day 1/baseline and thereafter). The first loading dose of the study is administered at the site. The loading dose is double the intended dose for the first two days and is administered twice daily (BID) with 12 hour interval between dosing. Thereafter, starting on day 3, the dosing regimen consists of the intended dose once daily (QD) (see Table 1):
1. Day 1 (Baseline): loading dose of the drug (intended dose at 0 hour, at the site and intended dose at 12 hours). Total dose is twice the intended dose.
2. Day 2: loading dose of the study drug (intended dose at 0 hour and intended dose at 12 hours). Total dose is twice the intended dose.
3. Day 3: Intended/maintenance dose of the study drug.

Allowed previous standard of care treatment is kept stable throughout the study (including the follow-up period as defined herein).

PK Analysis
Pharmacokinetic Sub-Study (PK)—Ancillary Study Performed in Subset of Sites
Blood samples for PK analysis—24 h profile—are collected from subjects in the first cohort (0.5 mg/placebo) on week 4.

A single, pre-dose sample is collected from the first cohort (0.5 mg/placebo) on week 1 as part of steady state course assessment.

Population PK Study (PPK)
Blood samples for PPK evaluation are collected at weeks 2 and 8 from all subjects in all cohorts. A pre-dose sample and a single sample at post-dose time range within 0.5 to 6 hours are collected.

Pharmacogenetic Sub-Study
Blood samples for the pharmacogenetic sub-study are collected from all subjects who sign the separate informed consent form and upon Ethics Committee (EC) approval.

Allowed Concomitant Medications During Study
In general the dose of allowed concomitant medication is kept stable throughout the study (including the follow-up period). Any new medication/treatment for CD or dose increase not allowed by the protocol, throughout the study treatment period, results in major protocol violation and are regarded as a treatment failure. Decrease in dose or dose regiment, not allowed by the protocol, also results in major protocol violation.

CD surgery, biologic treatment or new immunosuppressive drugs, throughout the study treatment period, are regarded as treatment failure and results in early treatment discontinuation.

5-ASA Compounds
The use of 5-ASA compounds are kept stable throughout the study.

Antibiotics
The use of antibiotics for the treatment of Crohn's disease is kept stable throughout the trial. Managing acute infections (not related to Crohn's disease) is allowed.

Corticosteroids
The dose of oral corticosteroids remains stable throughout the study:
1. Oral systemic corticosteroids—no more than prenisolone 2.5 mg/day (or equivalent) increase or decrease compared to baseline.
2. Budesonide—no change is permitted compared to baseline.
3. IV or IM corticosteroid dose or corticosteroid enemas are not allowed.

Immunosuppresives
Immunosuppressive treatment allowed by the protocol (AZA/6MP/MTX) is kept stable throughout the study. Addition of new immunosuppressive drug is not allowed Other
1. Antidiarrehal drugs, analgesics, NSAIDs and topical preparations are allowed (including topical dermatological, ophthalmological or inhale steroids).
2. The use of probiotics is kept stable throughout the study.

Inclusion/Exclusion Criteria
Inclusion Criteria
Subjects must meet all the inclusion criteria to be eligible:
1. Males and females 18-75 years old (inclusive).
2. Subjects diagnosed with Crohn's disease for at least months prior to screening, which has been appropriately documented and supported by endoscopy or radiology (performed within 36 months prior to screening and after surgical resection), or surgery.
3. Moderate to severe Crohn's disease patients as determined by a CDAI score of 220-450 (inclusive).
4. Subjects with C-Reactive Protein (CRP) levels above 5 mg/L at screening or any time between screening to baseline, including at baseline, OR documented endoscopic evidence of mucosal ulcerations within 4 weeks prior to baseline.
   a. Evidence of mucosal ulcerations is defined as the presence of at least 2 ulcers ≥10 mm.
   b. Documentation includes the endoscopy report with supporting photo or video.
5. Subjects willing and able to provide written, informed consent.

Exclusion Criteria
Any of the following excludes the subject from entering the study:
1. Subjects with a diagnosis of Indeterminate Colitis:
2. Subjects with positive results on stool culture for enteric pathogens (Salmonella, Shigella, Yersinia, Campylobacter or Clostridia Difficile toxin assay), at screening.
3. Subjects who have had bowel surgery within the 3 months prior to screening or with planned elective surgery or hospitalization during the course of the study (that may interfere with study compliance or outcome).
4. Subjects with clinically significant Short Bowel Syndrome.
5. Subjects with clinically significant GI obstructive symptoms.
6. Subjects with intra-abdominal abscess.

7. Subjects with fistula with clinical or radiological evidence of abscess.
8. Subjects with ileostomy, colostomy or who receive parenteral nutrition.
9. Subjects with a clinically significant or unstable medical or surgical condition that, in the Investigator's opinion, would preclude safe and complete study participation, as determined by medical history, physical examinations, ECG, laboratory testing or imaging. Such conditions may include:
    a. A cardiovascular or pulmonary disorder that cannot be well-controlled by standard treatment permitted by the study protocol.
    b. Renal, metabolid or hematological diseases.
    c. Any form of acute or chronic liver disease.
    d. Known human immunodeficiency virus (HIV) positive status.
    e. Systemic infection at screening.
    f. A family history of Long-QT syndrome.
    g. A history of drug and/or alcohol abuse.
    h. A current major psychiatric disorder.
10. Subjects with a ≥2× upper limit of normal (ULN) serum elevation of either of the following at screening: ALT, AST, GGT, ALKP or direct bilirubin.
11. A QTc interval which is >500 msec (according to machine output), obtained from:
    a. Two ECG recordings at screening visit OR
    b. The mean value calculated from 2 baseline ECG recordings.
12. Subjects with history of any malignancy in the last year, prior to screening, excluding basal cell carcinoma.
13. Subjects treated with oral corticosteroids (e.g. prednisolone/budesonide), who have initiated this treatment within less than 4 weeks prior to screening.
14. Subjects treated with more than 20 mg/day of prednisolone (or equivalent) or budesonide >6 mg/day for CD at screening, or whose corticosteroid dosage regimen is not stable for at least 2 weeks prior to baseline. [stable dose defined as ≤2.5 mg prednisolone (or equivalent) increase or decrease, no change in budesonide and no IV or IM steroid administration, within the last 2 weeks prior to baseline].
15. Subjects treated with 5-ASA who are not on stable dose for at least 2 weeks prior to screening.
16. Subjects treated with antibiotics for CD who are not on a stable dose for at least 2 weeks prior to screening.
17. Subjects treated with 6-MP, AZA or MTX, who have initiated this treatment within 12 weeks prior to screening or who are not on a stable dose for at least 6 weeks prior to screening.
18. Subjects treated with Anti-TNFs within 4 weeks prior to screening [The percentage of subjects previously treated with anti-TNF drugs are limited to approximately 60% of subjects randomized for each cohort. All site principle investigators are notified by the Sponsor when the quota of previous treatment with anti-TNF drugs has been reached for each cohort].
19. Subjects treated with cyclosporine, tacrolimus, mycophenolate mofetil or thalidomide within 2 months prior to screening.
20. Subjects treated with natalizumab within 6 months prior to screening.
21. Subjects who have used any other investigational drugs within 3 months prior to screening.
22. Use of inhibitors of CYP3A4 within 2 weeks prior to base line visit (1 month for fluoxetine).
23. Use of amiodarone within 2 years prior to screening visit.
24. Women who are pregnant or nursing at the time of screening, or who intend to be during the study period.
25. Women of child-bearing potential who do not practice an acceptable method of birth control. Acceptable methods of birth control in this study are: surgical sterilization, intrauterine devices, oral contraceptive, contraceptive patch, long-acting injectable contraceptive, partner's vasectomy, a double-protection method (condom or diaphragm with spermicide).
26. A known drug hypersensitivity that would preclude administration of the study drug, such as hypersensitivity to: mannitol, meglumine or sodium stearyl fumarate.
27. Subjects unable to comply with the planned schedule of study visits and study procedures.

Withdrawal Criteria/Treatment Failure
1. At the direction of the investigator, a subject who fails to respond to the treatment protocol is withdrawn from the study.
2. Rescue therapy for Crohn's disease (any new medication/treatment or dose increase, not allowed by the protocol), throughout the study treatment period, results in major protocol violation and is regarded as a treatment failure.
3. CD Surgery, biologic treatment of new immunosuppressive drugs, throughout the study treatment period, is regarded as treatment failure and results in early treatment discontinuation.

Monitoring Plan and Safety Stopping Rules
In any of the events listed below, the subject's participation in the study is discontinued immediately. The subject is followed until resolution or stabilization of symptoms or lab abnormalities:
1. Any increase in ALT or AST to ≥3 times ULN, combined with either ≥1.5 times ULN elevation of INR or ≥2 times ULN elevation of total bilirubin.
2. Any increase in ALT or AST to ≥3 times ULN, with the appearance of worsening of fatigue, nausea, vomiting, right upper quadrant pain or tenderness, fever, rash, or eosinophilia.
3. Any increase in Alt or AST to levels ≥5 but <8 times ULN, which is persistent for ≥2 weeks of repeated measurements.
4. Any increase in ALT or AST to levels ≥8 times ULN.

Outcome Measures
Clinical Effect
The study exploratory efficacy outcome measures are chosen according to the draft EMEA guidelines for the treatment of active Crohn's disease/induction of remission (EMEA, 2007)
1. Proportion of subjects in clinical remission (total CDAI score <150) at weeks 4, 6, 8 and 12.
2. Proportion of subjects who respond to treatment (decrease from baseline of at least 100 points in CDAI score ore remission) at week 4, 6, 8 and 12.
3. Time to remission.
4. Time to response.
5. C-Reactive Protein (CRP) change from baseline at weeks 2, 4, 6, 8 and 12.
6. Fecal calprotectin change from baseline to weeks 2, 4, 6, 8 and 12.
7. Proportion of subjects with a decrease from baseline of at least 50% in the number of open draining fistulas.

Safety/Tolerability
1. Adverse events (AEs).
2. Clinical laboratory values.
3. Vital signs.
4. ECG.

5. Proportion of subjects who prematurely discontinue treatment.
6. Proportion of subjects who prematurely discontinue treatment due to AEs.
7. Time to premature treatment discontinuation.
8. Time to premature treatment discontinuation due to AEs.

Determination of the Highest Tolerable Dose

At any of the safety evaluations, the safety committee may determine that a Dose Limiting Toxicity (DLT) has been reached. Criteria for DLT are not predefined and are based solely on the safety committee's best medical judgment.

The highest tolerable dose is defined as the dose level below the dose at which no further escalation is permitted, according to the decision of the safety committee.

Pharmacokinetics/Population PK

Steady state parameters ($AUC_{tau}$, $C_{max}$ and $C_{min}$) are calculated for the 0.5 mg dose only (in a subset of sites)

The population approach is used to fit the plasma concentration-time data from all dose groups, if possible. The effect of different covariates on the pharmacokinetics of laquinimod is evaluated in the model (all sites, all cohorts).

Results 0.5 mg/day 0.5 mg/day oral dose of laquinimod in subjects with moderate to severe Crohn's disease (CDAI score of 220-450) reduces the symptoms of Crohn's disease in the subject, induces clinical response, induces and/or maintains clinical remission, and/or inhibits disease progression and/or disease complication in the subject. Specifically, the administration of the laquinimod reduces the subject's Crohn's Disease Activity Index score, lowers the subject's C-Reactive Protein level and/or fecal calprotein level, and/or reduces the number of open draining fistulas in the subject. Moreover, 0.5 mg/day oral dose of laquinimod in subjects with moderate to severe Crohn's disease lowers the subject's dependence on steroids.

1.0 mg/day 1.0 mg/day oral dose of laquinimod in subjects with moderate to severe Crohn's disease (CDAI score of 220-450) reduces the symptoms of Crohn's disease in the subject, induces clinical response, induces and/or maintains clinical remission, and/or inhibits disease progression and/or disease complication in the subject. Specifically, the administration of the laquinimod reduces the subject's Crohn's Disease Activity Index score, lowers the subject's C-Reactive Protein level and/or fecal calprotein level, and/or reduces the number of open draining fistulas in the subject. Moreover, 1.0 mg/day oral dose of laquinimod in subjects with moderate to severe Crohn's disease lowers the subject's dependence on steroids.

1.5 mg/day 1.5 mg/day oral dose of laquinimod in subjects with moderate to severe Crohn's disease (CDAI score of 220-450) reduces the symptoms of Crohn's disease in the subject, induces clinical response, induces and/or maintains clinical remission, and/or inhibits disease progression and/or disease complication in the subject. Specifically, the administration of the laquinimod reduces the subject's Crohn's Disease Activity Index score, lowers the subject's C-Reactive Protein level and/or fecal calprotein level, and/or reduces the number of open draining fistulas in the subject. Moreover, 1.5 mg/day oral dose of laquinimod in subjects with moderate to severe Crohn's disease lowers the subject's dependence on steroids.

2.0 mg/day 2.0 mg/day oral dose of laquinimod in subjects with moderate to severe Crohn's disease (CDAI score of 220-450) reduces the symptoms of Crohn's disease in the subject, induces clinical response, induces and/or maintains clinical remission, and/or inhibits disease progression and/or disease complication in the subject. Specifically, the administration of the laquinimod reduces the subject's Crohn's Disease Activity Index score, lowers the subject's C-Reactive Protein level and/or fecal calprotein level, and/or reduces the number of open draining fistulas in the subject. Moreover, 2.0 mg/day oral dose of laquinimod in subjects with moderate to severe Crohn's disease lowers the subject's dependence on steroids.

REFERENCES

1. PCT International Application Publication No. WO 2007/047863, published Apr. 26, 2007, international filing date Oct. 18, 2006.
2. PCT International Application Publication No. WO 2007/146248, published Dec. 21, 2007, international filing date Jun. 12, 2007.
3. Best W R, Becktel J M, Singleton J W, et al. Development of a Crohn's Disease Activity Index. Gastroenterology 1976; 70:439-444.
4. Best W R, Becktel J M, Singleton J W. Rederived values of the eight coefficients of the Crohn's Disease Activity Index (CDAI). Gastroenterology 1979; 77:843-6.
5. Chamouard P, Richert Z, Meyer N, Rahmi G. Diagnostic value of C-reactive protein for predicting activity. Clin Gastroenterol hepatol 2006; 4:882-887.
6. Colombel J F, Loftus E V Jr., Tremaine W J, et al. The safety profile of infliximab in patients with Crohn's disease: the Mayo clinic experience in 500 patients. Gastrolenterol 2004; 126:19-31.
7. Colombel J F, Sandborn W J, Rutgeerts P, Enns R, Hanauer S B, Panaccione R, Schreiber S, Byczkowski D, Li J, Kent J D, Pollack P F. Adlimumab for maintenance of clinical response and remission in patients with Crohn's disease: the CHARM trial. Gastroenterol 2007; 132(1):52-65.
8. Comi G, Pulizzi A, Rovaris M, Abramsky O, Arbizu T, Boiko A, Gold R, Havrdova E, Komoly S, Selmaj K W, Sharrack B, Filippi M, for the LAQ/5062 Study Group. Effect of laquinimod on MRI-monitored disease activity in patients with relapsing-remitting multiple sclerosis: a multicentre, radomised, double-blind, placebo-controlled phase IIB study. Lancet 2008; 371:2085-92.
9. Denis M A, Reenaers C, Fontaine F, Blaiche J, Louis E. Assessment of Endoscopic Activity Index and Biological Inflammatory Markers in Clinically Active Crohn's disease with Normal C-reactive Protein Serum Level. Inflamm Bowel Dis 2007; 13:1100-1105.
10. EMEA 2007. Points to consider on clinical investigation of medicinal products for the management of Crohn's disease. CPMP/EWP/2284/99 Rev.1.
11. Friedman S, Blumberg R S. Inflammatory Bowel Disease. In: Braunwald E., Fauci A S, Kasper D L, Hauser S L, Longo D L, Jameson J L, eds. Harrison's Principles of Internal Medicine. New York: McGraw-Hill Professional, 2001:1679-92.
12. Ghosh S, Goldin E, Gordon F H, et al. Natalizumab for active Crohn's disease. N. Engl J Med 2003; 348:24-32.
13. Guindi M and Riddell, RH (2004) "Indeterminate Colitis" J. Clin. Pathol. 57:1233-1244.
14. Hanauer S B, Feagan B G, Lichtenstein G R et al. Maintenance infliximab for Crohn's disease: the accent I randomised trial. Lancet 2002; 359.
15. Hendrickson B A, Gokhale R, Cho J H. Clinical aspects and pathophysiology of inflammatory bowel disease. Clin Microbiol Rev 2002; 15:79-94.

16. Hommes D W, Van Deventer S J H. Inflixmab therapy in Crohn's disease: safety issues. Neth J Med 2003; 61:100-104.
17. Jonsson S, Andersson G, Fex T, Fristedt T, Hedlund G, Jansson K, Abramo L, Fritzson I, Pekarski O, Runstrom A, Sandin H, Thuvesson I, Bjork A. Synthesis and biological evaluation of new 1,2-dihydro-4-hydroxy-2-oxo-3-quinolinecarboxamides for treatment of autoimmune disorders: structure-activity relationship. J Med Chem. 2004 Apr. 8; 47(8):2075-88.
18. Kasper D L, Braunwald E, Fauci A S, Hauser S L, Longo D L, Jameson J L, Loscalzo J. (2008). *Harrison's principles of internal medicine* (17th ed.). New York: McGraw-Hill Medical Publishing Division. ISBN 978-0-07-146633-9.
19. Kozuch P L, Hanauer S B. Treatment of inflammatory bowel disease: A review of medical therapy. World J Gastroenterol; 2008; 14(3):354-377.
20. Laquinimod Investigator's Brochure (IB), Ed. 4, Nov. 2007. Addendum No. 1. June, 2008, Supplement to Investigator's Brochure, Ed. 4, Nov. 2007.
21. Lund Research Center AB, Active Biotech Group, Sweden. The inhibitory activity of PNU-215062 on acute experimental autoimmune encephalomyelitis in the mouse and a comparison with the activity of roquinimex (PNU-212616). 9830161, Final Report February 1999.
22. Sandborn W J, Colombel J F, Enns R, Feagan B G, Hanauer S B, Lawrance I C, Panaccione, Sanders M, Schreiber S, Targan S, van Deventer S, Goldblum R, Despain D, Hogge G S, Rutgeerts. P; Natalizumab induction and maintenance therapy for Crohn's disease. N Engl J Med. 2005; 353(18):1912-25.
23. Sandborn W J, Feagan B G, Hanauer S B, et al. A review of activity indices and efficacy endpoints for clinical trials of medical therapy in adults with Crohn's disease. Gastroenterology. 2002; 512-530.
24. Schreiber S, Khaliq-Kareemi M, Lawrance I C, Thomasen OØ, Hanauer S B, McColm J, Bloomfield R, Sandborn W J; Maintenance therapy with centrolizumab pegol for Crohn's disease. N Engl J Med. 2007; 357:239-50.
25. Schreiber S, Rutgeerts P, Fedorak R N, et al. A randomized, placebo-controlled trial of certolizumab pegol (CDP870) for treatment of Crohn's disease. Gastroenterol 2005; 129:807-818.
26. Silverberg M S, Satsangi J, Ahmad T, Arnott I D, Berstein C N, Brant S R, Caprilli R, Colombel J F, Gasche C, Geboes K, Jewell D P, Karban A, Loftus Jr E V, Perla A S, Riddell R H, Sachar D B, Schreiber S, Steinhart A H, Targan S R, Vermeire S, Warren B F. Toward an integrated clinical, molecular and serological classification of inflammatory bowel disease: Report of a Working Party of the 2005 Montreal World Congress of Gastroenterology. Can J Gastroenterol. 2005; 19 Suppl A:5-36.
27. Solem C A, Loftus E V Jr., Tremaine W J, et al. Correlation of C-reactive protein with clinical, endoscopic, histologic, and radiographic activity in Inflammatory Bowel disease. Inflamm Bowel Dis. 2005; 11(8):707-12.
28. Sweetman S C, Blake P S, McGlashan J M, Neathercoat G C, editors. Martindale: The complete drug reference. London: Pharmaceutical Press. Electronic version, (Edition 35 [2006]).
29. Targan S R, Feagan B G, Fedorak R N, Lashner B A, Panaccione R, Present D H, Spehlmann M E, Rutgeerts P J, Tulassay Z, Volfova M, Woolf D C, Hernandez C, Bornstein J, Sandborn W J; Natalizumab for the treatment of active Crohn's disease: result of the ENCORE Trial. Gastrolentology. 2007; 132(5):1672-83.
30. Targan S R, Hanauer S B, van Deventer S J et al. A short-term study of chimeric monoclonoal antibody cA2 to tumor necroseis factor alpha for Crohn's disease. N. Engl J Med 1977; 337:1029-35.
31. Thomas C W Jr., Weinshenker B G, Sandborn W J. Demyelination during anti-tumor necrosis factor alpha therapy with infliximab for Crohn's disease. Inflamm Bowel Dis 2004; 10:28-31.
32. Van Assche G, Van Ranst M, Sciot R, et al. Progressive multifocal leukoencephalopathy after natalizumab therapy for Crohn's disease. N Engl J Med 2005; 353:362-8.
33. Vermeire S, Noman M, Van Assche G, et al. Autoimmunity associated with anti-tumor necrosis factor alpha treatment in Crohn's disease: a prospective cohort study. Gastroenterol 2003; 125:32-9.
34. Wen Z, Fiocchi C. Inflammatory bowel disease: autoimmune or immune-mediated pathogenesis? Clin Develop Immunol 2004; 11:195-204.
35. Wu, George. Crohn Disease, Emedicine, 2007.

What is claimed is:

1. A method of treating a subject suffering from Crohn's disease, the method consisting essentially of periodically administering to the subject an amount of laquinimod or pharmaceutically acceptable salt thereof effective to treat the subject.

2. The method of claim 1, wherein the amount of laquinimod is effective to reduce a symptom of Crohn's disease in the subject, induce clinical response, induce or maintain clinical remission, inhibit disease progression, or inhibit a disease complication in the subject.

3. The method of claim 1, wherein the amount of laquinimod is effective to reduce the Crohn's Disease Activity Index score of the subject, lower the C-Reactive Protein level of the subject, lower the fecal calprotein level of the subject, or reduce the number of open draining fistulas in the subject.

4. The method of claim 3, wherein the Crohn's Disease Activity Index score of the subject is reduced by at least 100 points.

5. The method of claim 3, wherein the Crohn's Disease Activity Index score of the subject is reduced to under 150.

6. The method of claim 3, wherein the number of open draining fistulas in the subject is decreased at least 50% as compared to prior initiation of the periodic administration.

7. The method of claim 1, wherein the periodic administration is oral.

8. The method of claim 1, wherein the amount is administered by a unit dose of 0.5 mg of laquinimod.

9. The method of claim 1, wherein the periodic administration is daily administration.

10. The method of claim 9, wherein the amount of laquinimod is 0.5-2.0 mg/day.

11. The method of claim 10, wherein the amount of laquinimod is 1.0 mg/day.

12. The method of claim 10, wherein the amount of laquinimod is 1.5 mg/day.

13. The method of claim 10, wherein the amount of laquinimod is 2.0 mg/day.

14. The method of claim 1, wherein a loading dose of an amount different from the intended dose is administered for a period of time at the start of the periodic administration.

15. The method of claim 14, wherein the loading dose is double the amount of the intended dose.

16. The method of claim 14, wherein the loading is administered for two days at the start of the periodic administration.

17. The method of claim 1, wherein the subject had active moderate to severe Crohn's disease prior to the administration of laquinimod.

18. The method of claim 1, wherein the subject had a Crohn's Disease Activity Index score of 220-450 prior to the administration of laquinimod.

19. The method of claim 1, wherein the subject had a C-Reactive Protein level of above 5 mg/L prior to the administration of laquinimod.

20. The method of claim 17, wherein diagnosis of the subject prior to administration excluded Indeterminate Colitis.

21. The method of claim 17, wherein diagnosis of the subject prior to administration excluded Ulcerative Colitis.

22. The method of claim 1, wherein the periodic administration continues for 8 weeks or more.

23. The method of claim 1, wherein the laquinimod is in the form of laquinimod sodium.

24. The method of claim 1, wherein the subject is a human.

* * * * *